United States Patent [19]

Harris

[11] Patent Number: 5,308,340
[45] Date of Patent: May 3, 1994

[54] MULTIPLE DOSE INJECTION PEN

[75] Inventor: Dale C. Harris, Fairland, Ind.

[73] Assignee: Eli Lilly and Company, Indianapolis, Ind.

[21] Appl. No.: 79,307

[22] Filed: Jun. 17, 1993

Related U.S. Application Data

[60] Division of Ser. No. 960,314, Oct. 13, 1992, Pat. No. 5,226,895, which is a continuation of Ser. No. 361,132, Jun. 5, 1989, abandoned.

[51] Int. Cl.[5] ............................................. A61M 5/00
[52] U.S. Cl. ................................... 604/208; 604/211; 604/218
[58] Field of Search ............... 604/192, 193, 201, 203, 604/207–211, 218, 224, 246

[56] References Cited

U.S. PATENT DOCUMENTS

| | | | |
|---|---|---|---|
| 3,002,517 | 12/1959 | Pitton | 132/85 |
| 3,232,117 | 2/1966 | Gilmont | 73/425.6 |
| 3,613,952 | 10/1971 | Gilmont | 222/43 |
| 3,815,785 | 6/1974 | Gilmont | 222/46 |
| 3,884,230 | 5/1975 | Wulff | 128/221 |
| 4,096,751 | 6/1978 | Withers et al. | 73/425.6 |
| 4,275,729 | 6/1981 | Silver et al. | 128/218 C |
| 4,367,739 | 1/1983 | LeVeen et al. | 128/236 |
| 4,395,921 | 8/1983 | Oppenlander | 73/864.1 |
| 4,413,760 | 11/1983 | Paton | 222/309 |
| 4,475,905 | 10/1984 | Himmelstrup | 604/208 |
| 4,498,904 | 2/1985 | Turner et al. | 604/211 |
| 4,592,745 | 6/1986 | Rex et al. | 604/211 |
| 4,710,179 | 12/1987 | Haber et al. | 604/211 |
| 4,865,591 | 9/1989 | Sams | 604/186 |
| 4,883,472 | 11/1989 | Michel | 604/208 |
| 4,936,833 | 6/1990 | Sams | 604/232 |
| 4,973,318 | 11/1990 | Holm et al. | 604/208 |
| 5,092,842 | 3/1992 | Bechtold et al. | 604/135 |

FOREIGN PATENT DOCUMENTS

| | | | |
|---|---|---|---|
| 268191 | 5/1988 | European Pat. Off. | A61M 5/28 |
| 1632032 | 11/1977 | Fed. Rep. of Germany | B67D 1/08 |
| 3031830 | 3/1982 | Fed. Rep. of Germany | G01F 11/04 |
| 8804656.7 | 9/1988 | Fed. Rep. of Germany | A61B 5/14 |
| 250467 | 10/1987 | German Democratic Rep. | A61M 5/20 |
| WO 87/02895 | 5/1987 | PCT Int'l Appl. | A61M 5/24 |
| WO 88/07874 | 10/1988 | PCT Int'l Appl. | A61M 5/315 |

Primary Examiner—John D. Yasko
Assistant Examiner—Corrine Maglione
Attorney, Agent, or Firm—Douglas J. Taylor; Leroy Whitaker

[57] ABSTRACT

The present invention relates to a hypodermic syringe having the same general appearance as a pen which is specifically adapted to provide for multiple measure injections of materials such as insulin or human growth hormone.

29 Claims, 3 Drawing Sheets

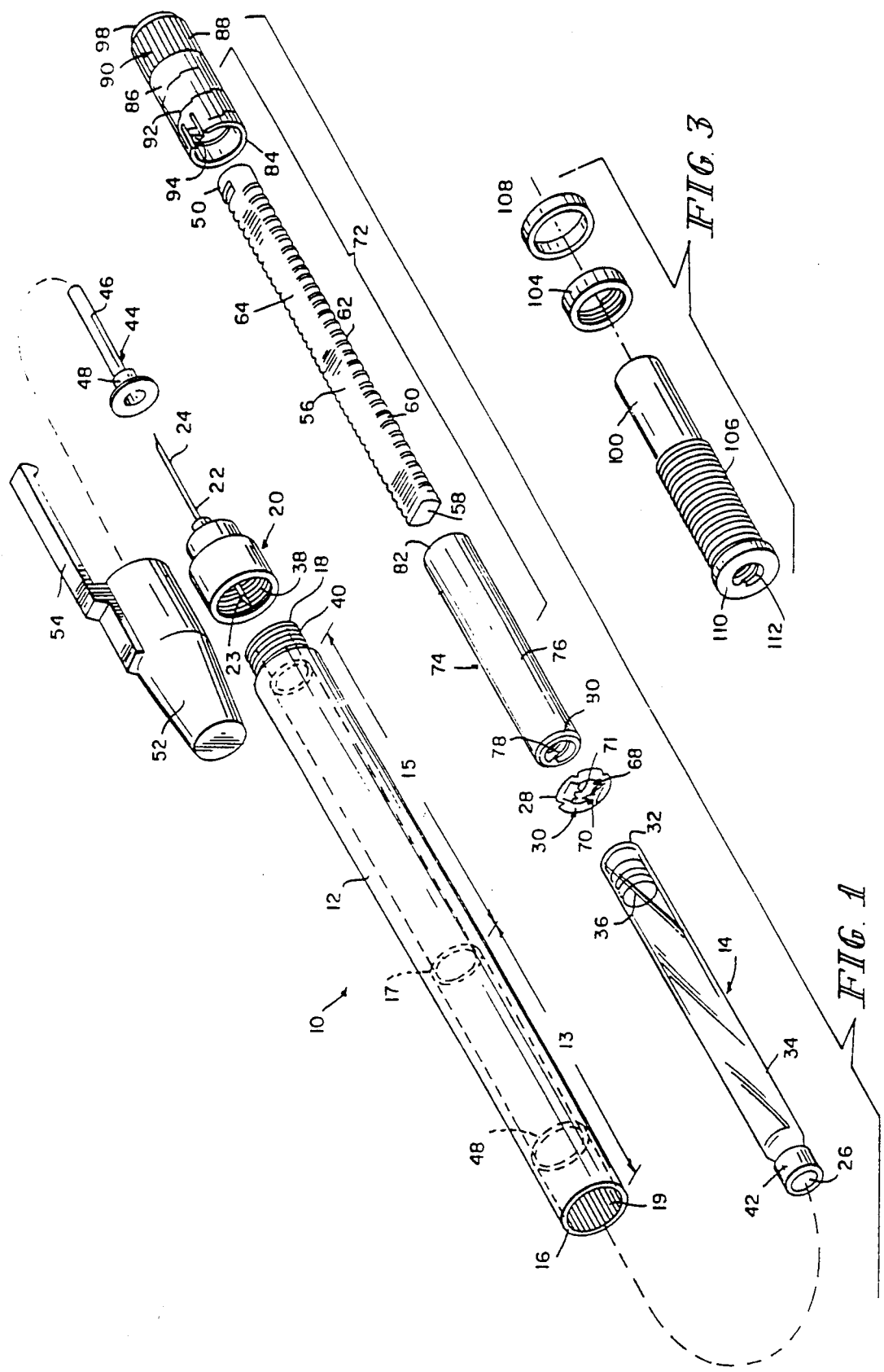

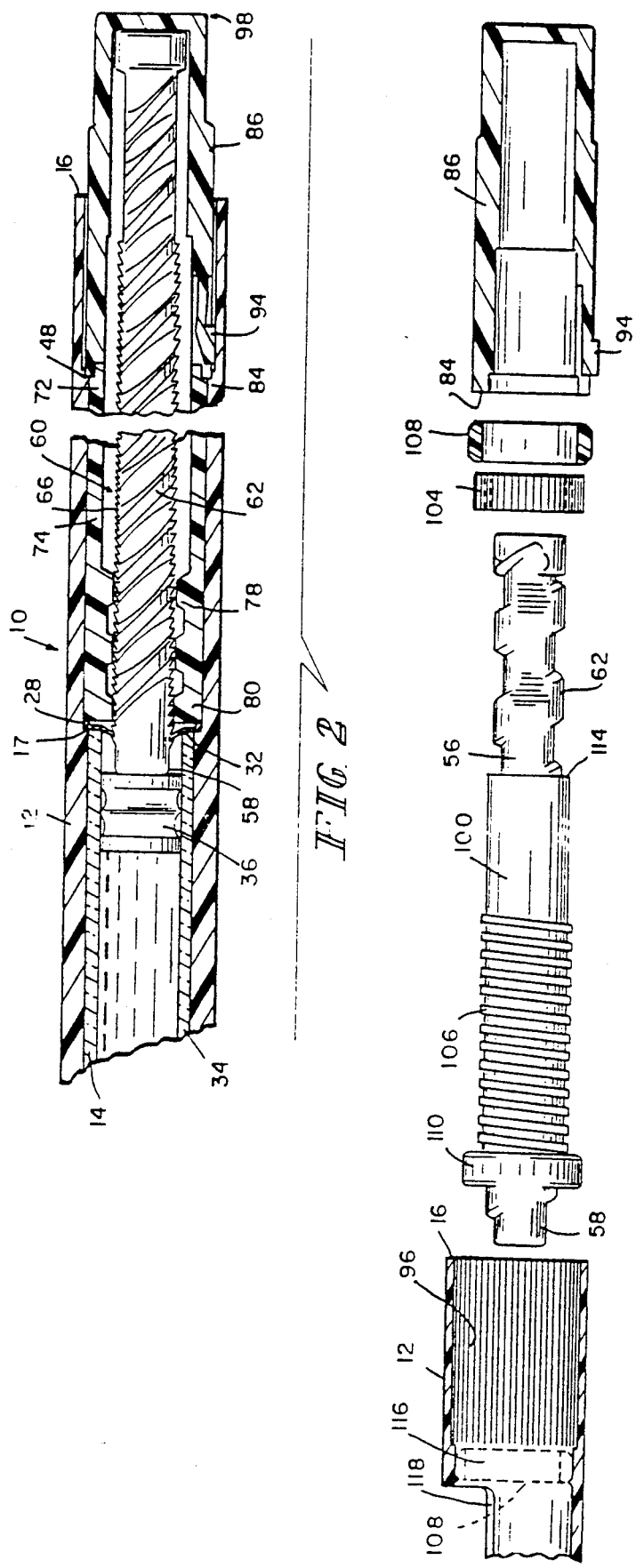

MULTIPLE DOSE INJECTION PEN

This application is a division of application Ser. No. 07/960,314, filed Oct. 13, 1992, now U.S. Pat. No. 5,226,895 which is a continuation of application Ser. No. 07/361,132, filed Jun. 5, 1989, now abandoned.

BACKGROUND OF THE INVENTION

The present invention relates generally to devices suitable for use in dispensing a measured amount of liquid material from a container. The invention particularly relates to a hypodermic syringe having the same general appearance as a pen which is specifically adapted to provide for multiple measured injections of materials such as insulin or human growth hormone.

Diabetics and others frequently find themselves in situations where the assistance of a health professional to administer the subcutaneous or intra muscular injection of measured amount of a liquid agent is generally not available. In such situations such persons need to have a low cost syringe which does not require the assistance of a health professional to achieve the desired measure of accuracy. It is often the case that such persons require more than one dose per day, each dose being of a somewhat different volume. Dispensers of this general type are known which have the general appearance of a pen or mechanical pencil The dispenser is typically large enough to hold several such doses, yet it is small enough to fit conveniently in one's pocket or purse. Examples of such devices are to be found in U.S. Pat. Nos. 4,413,760; 4,498,904; and 4,592,745. Additional examples are shown in PCT International Publications WO 87/02895 and WO 88/07874.

In devices of this class, a container of the liquid is provided having a closed first end adapted to be penetrated by a needle assembly so as to permit the liquid in the container to pass out the closed first end for subcutaneous or intra muscular injection. The second end of the container is generally closed by a piston. To prevent tampering or reuse of the liquid container, the piston is generally designed such that a pushing force can be applied to the piston to reduce the liquid-holding volume of the container, but no feature is presented which would be suitable for pulling on the piston so as to enlarge the liquid-holding volume of the container.

An elongated member in the nature of a plunger rod is received within the housing for exerting a force on the piston closing the second end of the container. A means is provided for measuring the distance which the plunger rod travels to determine the decrease in volume of the liquid container which causes the dispensing of the liquid within the container. It has generally been recognized that the dispenser should have some feature which would allow the rod to only travel in a single direction toward the piston thereby preventing any action on the part of the rod which might permit an enhancement of the volume of the liquid container. A safety cover is generally provided over a needle assembly attached to the closed end of the container.

While the prior art pen-style syringes have met with some success, certain shortcomings have also been observed. In some prior art pens, the adjustment of the dose to be injected, once made, cannot be accurately diminished to a smaller value. This results in an unnecessary waste of the medicating liquid within the syringe. In some prior art pens, the indication of dose is difficult to read. Prior art pens have sometimes required the patient to read two scales and/or to do some computations in order to determine the dosage delivered. Further, most prior art devices are specifically intended for repeated use generally by substitution of containers within the syringe which can contribute to the unethical use of the syringe in connection with non-prescribed substances.

SUMMARY OF THE INVENTION

In order to overcome these and other shortcomings of the prior art, a syringe constructed in accordance with the present invention includes a housing for holding a container of liquid similar to that known in the prior art. A plunger rod is received within the housing for exerting a force on a piston closing a second end of the container. The plunger rod has a non-cylindrical cross-section with a first surface including threads and a second surface which can, optionally, include a line of ratchet teeth. A collar is received within the housing adjacent to the container second end for permanently retaining the container of liquid within the housing. The collar has a non-cylindrical opening corresponding generally to the cross-section of the plunger rod. The plunger rod passes through the non-cylindrical opening and is prevented from rotating with respect to the housing by the collar. A means on the collar engages the second surface of the plunger rod for restricting movement of the plunger rod away from the container of liquid.

A hollow cap envelops the plunger rod end opposite the container of liquid. A skirt of the hollow cap extends inside the housing. The cap includes a threaded interior surface which movably engages the plunger rod for calibrated adjustment relative thereto. The calibrated adjustment permits one to both increase and decrease the amount of liquid sought to be injected from the pen. A stop is Provided within the housing and a distal facing surface is provided on the hollow cap for contacting the stop upon linear movement of the cap and plunger rod as a unit toward the container to dispense liquid therefrom.

The apparatus as a whole is constructed from inexpensive materials and is adapted for machine assembly which contributes directly to a very low manufacturing cost thereby permitting the apparatus as a whole to be disposable. As indicated previously, the adjustment of the dose can be increased and decreased thereby diminishing any waste of the medicating liquid. The dose indication feature is simply and directly read thereby providing for a more accurate and cost effective use of the medicating liquid dispensed from the apparatus. Additional features and advantages will become apparent to those skilled in the art from the following detailed discussion of preferred embodiments exemplifying the best mode of carrying out the invention as presently perceived. The detailed description particularly refers to the accompanying figures.

BRIEF DESCRIPTION OF DRAWINGS

FIG. 1 is an exploded perspective view of one embodiment of a syringe in accordance with the present invention.

FIG. 2 is a sectional detail view of the syringe shown in FIG. 1 showing the dosage adjustment features.

FIG. 3 is an exploded perspective view of an alternative embodiment for a portion of the hollow cap including a maximum dosage restriction feature.

FIG. 4 is an elevation view of the alternative embodiment shown in FIG. 3 partially assembled.

DESCRIPTION OF THE PREFERRED EMBODIMENTS

Figure 5:
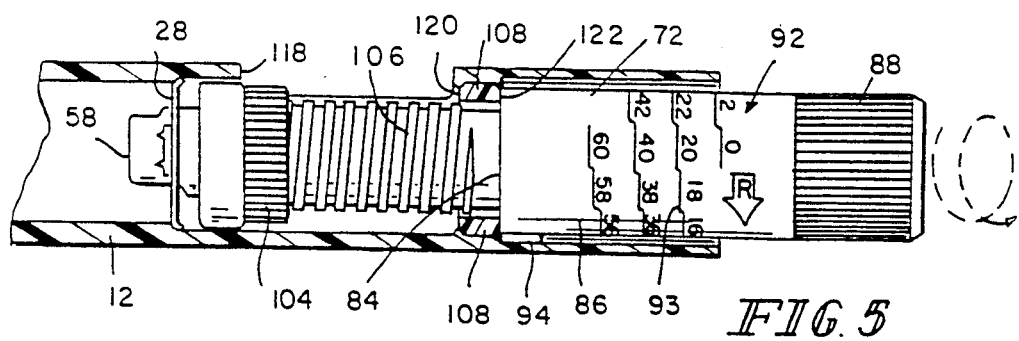
FIGS. 5-9 are elevation views partially broken away of the embodiment shown in FIG. 4 in five different positions to illustrate the dose restriction features of the invention.

A syringe 10 in accordance with the present invention is shown in FIGS. 1 and 2 to include a housing 12 which is adapted to receive a container 14 of liquid within a distal region 15 situated between the distal end 18 and a first shoulder 17. A proximal region 13 between the first shoulder 17 and proximal end 16 is adapted to receive the adjustment apparatus hereinafter described. The proximal region 13 includes a ribbed portion 19 which aids in the calibration and delivery of an accurate dose from the syringe. The distal end 18 of the housing 12 is adapted to receive a needle assembly 20 including a double-ended needle 22 having a distal end 24 which is adapted to permit subcutaneous or intra muscular injection and a proximal end 23 adapted to penetrate the rubber tip cover 26 of container 14. The container 14 is secured within the housing 12 by collar 28 which has an outer diameter providing an interference fit with the inside wall of the proximal portion 13 of housing 12 and forward face 30 intended to abut the proximal end 32 of container 14 adjacent first shoulder 17. The container 14 is shown to generally comprise a cylindrical envelope 34 including a piston 36 initially positioned near the proximal end 32 of the container 14 but movable with respect to the cylindrical wall 34 so as to define a variable liquid-containing volume for the container 14.

After the container 14 is situated within the housing 12 and retained in position by collar 28, the needle assembly 20 can be engaged on the distal end 18 of housing 12 by an appropriate securing means such as threads 38 on an inner surface of the needle assembly 20 engaging threads 40 on an outer distal surface of housing 12. Upon full engagement of the needle assembly 20 to the housing 12, a proximal end 23 of needle 22 penetrates the rubber portion 26 of the end cap 42 of container 14 thereby providing a pathway for liquid within the container 14 to be dispensed through needle 22.

A safety shield 44 including a sheath portion 46 and an engagement portion 48 is frictionally engaged on the needle assembly 20 to safely shield the needle from improper use. A covering element 52 including a clip 54 is used to enclose the distal end of the housing 12, needle assembly 20, and safety shield 44. The clip 54 cooperates with the sidewall of housing 12 to provide a convenient means for holding the syringe 10 in a pocket.

The syringe also includes a plunger rod 56 having a distal end 58 for contacting piston 36 of container 14. The plunger rod 56 has a noncylindrical cross-section with a first surface 60 of larger radial dimension which includes threads 62, and a second surface 64 of smaller radial dimension. The plunger rod 56 is received within the non-cylindrical opening 68 of collar 28. The interference relationship between the noncylindrical opening 68 of collar 28 and the noncylindrical cross-section of plunger rod 56 prevents rotation of the plunger rod 56 within the housing 12.

An inner surface 70 of collar 28 can include prongs 71 as shown in FIG. 1 which engage and dig into surface 64 of the plunger rod 56 to restrict movement of the plunger rod toward the proximal end 16 of housing 12. The prongs 71 on the inner surfaces 70 of collar 28 permit movement of the plunger rod 56 toward the distal end of the syringe 10 so as to cause the piston 36 to move within container 14 so as to diminish the volume of the container. Alternatively, the second surface 64 can include a line of ratchet teeth 66 as shown in FIG. 2. The ratchet teeth 66 can interact with the inner surfaces 70 of collar 28 even in the absence of prongs to restrict rearward movement of the plunger rod 56.

A hollow two-piece cap 72 is provided which envelopes substantially all of plunger rod 56 including proximal end 50. The cap 72 includes a distal portion 74 and a proximal portion 86 which can be manufactured separately for simplicity. The distal portion 74 comprises a generally cylindrical tube 76 having a threaded inner surface 78 at a distal end 80 thereof. The proximal portion 86 is of slightly greater outside diameter than distal portion 74. A proximal end 82 of distal portion 74 is fixed to a distal end 84 of the proximal portion 86 of cap 72 thereby forming a perimeteral distal end facing surface. A proximal end 88 of the proximal portion 86 protrudes from housing 12 at all times and can include ribs or serrations 90 adapted to permit easy adjustment of the volume to be injected using the syringe 10. The cap 72 includes indicia 92 providing a visual indication of the measured amount of liquid to be injected and includes a radially projecting tang 94 which interacts with a grooved interior 19 of housing 12. The tang 94 functions to provide an audible and tactile indication of the amount or degree of rotational movement of cap 72 with respect to housing 12. The tang 94 also aids linear movement of cap 72 with respect to housing 12 under the application of a force normal to the proximal end 98 of cap 72.

In operation, one desiring to inject a measured amount of liquid would first grasp the housing 12 in one hand and the ribbed portion 90 of cap 72 in the other. One would then rotate cap 72 in a counter-clockwise direction causing the threads 78 of cap 72 to travel along the threaded portion 62 of rod 56. This rotation would not cause displacement of the rod 56 with respect to the housing 12, but would back the distal end 84 of the proximal cap portion 86 away from stop shoulder 48 on the inside of housing 12. The counter-clockwise rotation of the cap 72 would also expose an increasing amount of indicia 92 above the proximal end 16 of the housing 12.

When used in connection with the dispensing of insulin, the indicia 92 is preferably denominated in international units. Other direct calibration scales can be used with other medications so that no computations are necessary to specify the desired dosage to be delivered The dose scale provided by the indicia 92 is read directly at the end of the proximal end 16 of the housing 12. The dose corresponds to the number corresponding to the last exposed step in the stepped line 93. In order that the indicia 92 can be calibrated in international units or equivalent direct measures of the medication in the container 14, the solutions or suspensions contained in the container 14 are preferably concentrated or diluted to optimize the potency of the medication so as to produce the desired physiological response in coordination with the scale adopted for in indicia 92. In the event that one would turn the cap 72 too far, it can also be rotated clockwise to diminish the dosage to be delivered without effecting any change in position of the rod 56 relative to the housing 12.

When the cap 72 has been positioned to the desired dosage as measured by the indicia 92, the safety shield 44 and cover 52 are removed, and the syringe 10 is positioned for injection. A Pressure is applied to end 98 of cap 72 causing it to move linearly toward the distal end 18 of housing 12 until a shoulder defined by a radially exposed portion of distal end 84 contacts stop 48. The movement of the cap 72 causes an identical movement of plunger rod 56 past collar 28, and movement of piston 36 within container 14 so as to dispense the liquid therefrom. The needle 22 can then be withdrawn and the safety shield 44 and cover 52 replaced.

FIG. 3 is a perspective view showing a modified distal portion 100 of cap 72 as well as a follower 104 which is adjustable with respect to the threaded outer surface 106 of the distal cap portion 100 and a barrier element 108 which is secured within an upper portion of housing 12. The distal end 110 of the distal portion 100 has a diameter substantially equivalent to that of distal portion 74 and has internal threads 112 identical with threads 78 of distal portion 74.

During the assembly from the relative position shown in FIG. 4, the follower 104 is threaded on threads 106 of cap distal portion 100. The barrier element 108 is then slipped over the distal cap portion 100, and the plunger rod 56 is inserted within the distal portion 100 sufficiently far to permit engagement between the plunger rod 56 and the collar 28 when the apparatus is fully assembled. The distal end 84 of the proximal portion of the cap 86 is then joined to the Proximal end 114 of distal portion 100. The two cap portions 86 and 100 can be bonded by a conventional means such as ultrasonic welding or solvents or the like. The assembly is then pushed inside housing 12 until barrier element 108 is situated at the location 116 shown in phantom. The barrier element 108 is then fixed to housing 12 again using solvents, ultrasonic welding, or other conventional techniques. It will be noted that housing 12 now includes a side opening 118 which was not present in FIG. 2, which side opening provides access to follower 104 so as to permit adjustment of the follower 104 along threads 106.

The operation of the embodiment shown in FIGS. 3 and 4 can best be understood by considering FIGS. 5 through 9. FIG. 5 illustrates a syringe 10 in accordance with the present invention in its initial assembled position. The distal end 58 of the plunger rod 56 is shown projecting slightly beyond collar 28. While the end 58 would normally be seated against a rear surface of a piston 36 as shown in FIG. 2, the container of liquid 14 and piston 36 have been omitted for the sake of clarity in illustrating the motion of plunger rod 56. It will be appreciated that the position of the plunger rod shown in FIG. 5 is substantially identical with that shown in FIG. 2, that is, the plunger rod extends within cap 72 throughout substantially the whole length of the cap.

Comparing FIGS. 5 to FIG. 9, it will be noted that follower 104 has been threaded on threaded portion 106 until contacting the distal end 110 of the distal cap portion 100. Barrier element 108 is fixed within housing 12 so that a distal edge 120 of barrier element 108 is substantially flush with the proximal edge of window 118. The proximal edge 122 of barrier element 108 forms a stop against which the distal end 84 of the proximal portion 86 of cap 72 abuts.

Figure 6:
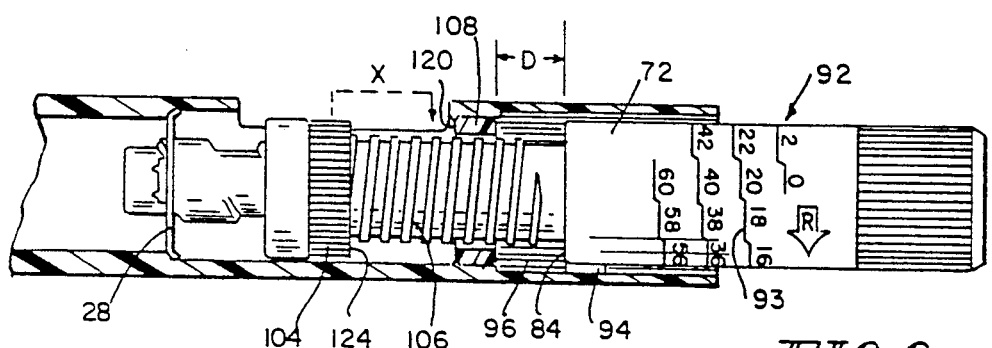

In order to dispense a measured amount of liquid, the serrated portion 88 of cap 72 is grasped and rotated in the direction of arrow cap R from the position shown in FIG. 5 to the position shown in FIG. 6. This rotation has the effect of causing the distal facing surface 84 to move rearward through a distance D. The rotating motion of the cap causes tang 94 to traverse linear markings 96 thereby giving an audible and tactile sensation of the rotation which can be correlated with the number of units of the particular medicament being dispensed. This rearward motion also exposes a greater portion of the indicia 92 which can include numbers also indicative of the dosage being prepared for delivery As previously indicated with respect to the embodiment shown in FIGS. 1 and 2, if cap 72 has been rotated too far, it can be rotated in the opposite direction to diminish the required dose.

A special feature present in the embodiments shown in FIGS. 3 through 9 which is not present in the embodiment shown in FIGS. 1 and 2 is the presence of follower 104 which can be adjusted to any position along threads 106. The principle function of follower 104 is to set a maximum allowable dose where the syringe is going to be used by persons who may have difficulty remembering the proper dosage, or may have some other physical disability which does not permit them to appreciate fully the meaning of the indicia 92. In such a circumstance, the cap 72 can first be rotated to the desired maximum measured value illustrated as an arbitrary position in FIG. 6. Next, the follower 104 is rotated through distance X from the position shown in FIG. 6 to the position shown in FIG. 7. In this position, the upper edge 124 of follower 104 abuts distal edge 120 of barrier element 108. Preferably the engagement between follower 104 and threads 106 is sufficiently tight such that follower 104 is moved only with some difficulty, or at least, the follower 104 is not likely to move merely under the influence of vibration or the like.

Figure 7:
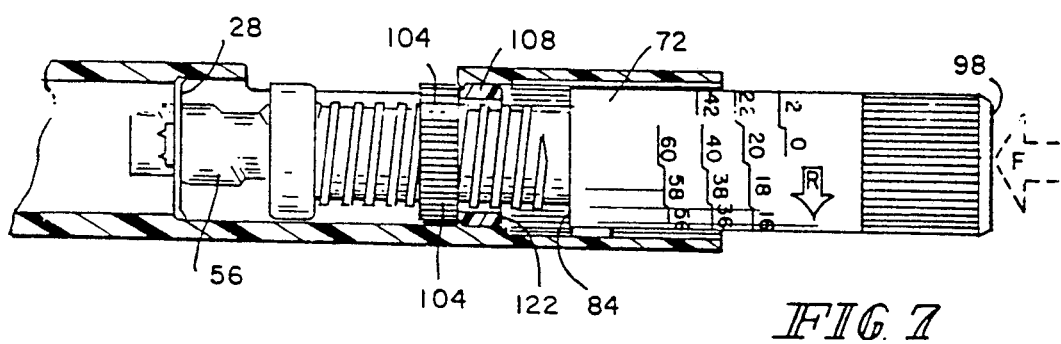

With the follower 104 set in the position shown in FIG. 7, the cap 72 can be rotated back to its original position. This rotation back to the starting position, or zero, will not cause any movement of the plunger rod 56 with respect to the collar 28 and hence no dispensing of liquid will take place. Alternatively, a force can be applied to the proximal end 98, as shown by arrow F, thereby moving the cap 72 and plunger rod 56 from the position shown in FIG. 7 until edge 84 once again contacts edge 122 of barrier element 108 thereby assuming the position shown in FIG. 8. It will be noted that with the force F applied to proximal end 98, the cap 72 and plunger rod 56 have both moved linearly through a distance L which is identical to the distance D shown in FIG. 6. The motion of the plunger rod 56 causes a forward motion of plunger 36 as shown in FIG. 2 to dispense the liquid within container 14 as previously discussed.

Figure 8:
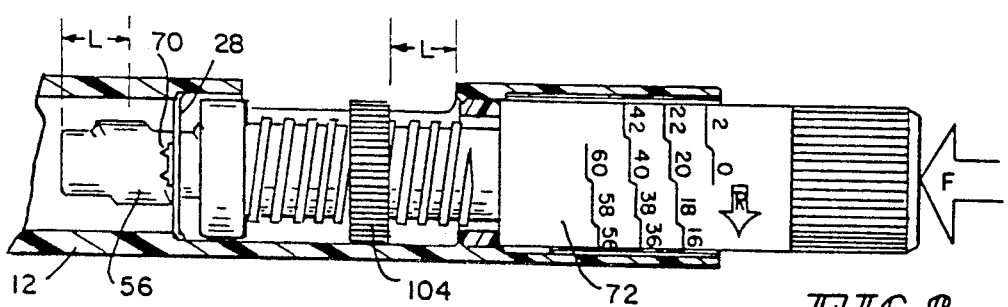
Figure 9:
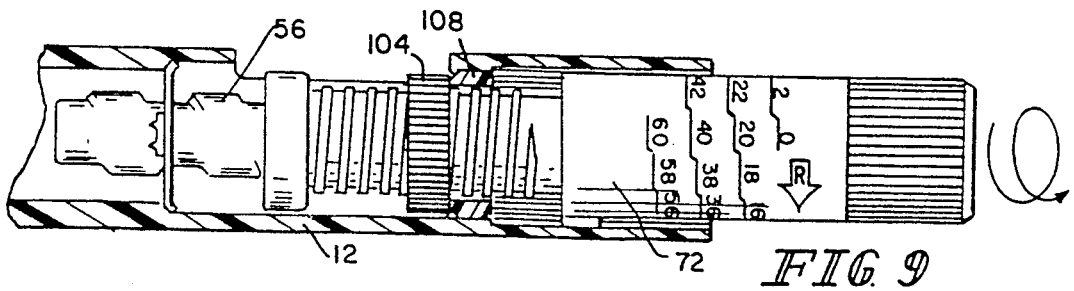

The syringe 10 may then be stored in the position shown in FIG. 8 until it is next needed for use. The edges 70 of collar 28 prevent any relative movement between the housing 12 and plunger rod 56 merely due to vibration or shock. When it is necessary to again use the syringe one again rotates cap 72 in the direction R from the position shown in FIG. 8 toward the position shown in FIG. 9. The follower 104 now limits the motion which can take place to something significantly less than that which could have been achieved before the follower 104 was moved from the position shown in FIG. 6. The rotating motion of cap 72 relative to housing 12 does not cause any relative motion between housing 12 and plunger rod 56. It will be appreciated that while follower 104, set in the position shown in FIGS. 7 through 9, limits the maximum dose which might be delivered, a smaller dose could be delivered if the cap 72 were not rotated to the position where follower 104 abutts barrier element 108.

Although the invention has been described in detail with reference to the illustrated preferred embodiments, variations and modifications exist within the scope and spirit of the invention as described and as defined in the following claims

I claim:

1. An improved means for adjustment of the dosage of liquid to be injected from a syringe having a housing for receiving a container of liquid, the container of liquid having a closed first end and a piston closing a second end of the container, the housing having a proximal end and a distal end, the distal end being adapted to receive an injection needle assembly for permitting liquid to pass out of the container first end, a plunger rod, having a non-cylindrical cross-section with a first surface, including threads, and a second surface, received within the housing for exerting a force on the piston closing the container second end, the improvement comprising:

first means received within the housing adjacent the container second end for preventing rotation of the plunger rod in relation to the housing;

second means engaging a second surface of the plunger road for restricting movement of the plunger rod toward the housing proximal end, third means used to adjust the dosage of liquid to be injected from the syringe, which means rotatably engages a first surface of the plunger road for calibrated axial movement with respect to the plunger rod and housing toward the housing proximal end, fourth means fixed with respect to the housing for stopping any movement of the third means toward the housing distal end at a fixed position relative to the housing, and limit means for limiting the maximum calibrated movement of the third means.

2. The improvement of claim 1 wherein the first means comprises a collar received within the housing adjacent the container second end, the collar having a non-cylindrical opening corresponding generally to the cross-section of the plunger rod for preventing rotation of the plunger rod with respect to the housing.

3. The improvement of claim 2 wherein the collar comprises a radial outside surface frictionally engaging an inside surface of the housing, and a distal end surface contacting the container of liquid for maintaining the container in fixed position with respect to the housing.

4. The improvement of claim 2 wherein the second means comprises engaging means included within the collar non-cylindrical opening and engaging a second surface on the plunger rod for restricting movement of the plunger rod toward the housing proximal end.

5. The improvement of claim 1 wherein the second means comprises engaging means engaging a second surface on the plunger rod for restricting movement of the plunger rod toward the housing proximal end.

6. The improvement of claim 5 wherein the engaging means comprises a pair of opposed edges situated on opposite sides of the plunger rod each engaging a surface on the plunger rod so as to prevent movement of the plunger rod toward the housing proximal end.

7. The improvement of claim 1 wherein the third means comprises a hollow cap enveloping the plunger rod end opposite the container and extending outward from the housing proximal end, the cap having a threaded interior surface movably engaging the first threaded surface of the plunger rod for calibrated adjustment relative thereto.

8. The improvement of claim 7 wherein the hollow cap further comprises a flexible member projecting outward from the cap and the housing further comprises a grooved interior surface, said flexible member engaging said grooved interior surface of the housing such that the calibrated relative adjustment causes sensible movement of the flexible member.

9. The improvement of claim 7 wherein the limit means comprises a threaded portion on an outer surface of the hollow cap and a follower adjustibly positioned on the threaded outer surface portion of the cap.

10. The improvement of claim 9 wherein the limit means further comprises a barrier element fixed with respect to the housing for limiting the length of movement of the hollow cap relative to the housing by contacting the adjustibly positioned follower.

11. The improvement of claim 1 wherein the third means comprises a hollow cap enveloping the plunger rod end opposite the container and extending outward from the housing proximal end, the cap engaging the plunger rod and having a distal end facing surface for contacting a stop fixed with respect to the housing upon movement of the cap and plunger rod toward the housing distal end.

12. The improvement of claim 11 wherein the distal end facing surface comprises the distal end of the cap, and the stop comprises a land within the housing situated to contact the distal end of the cap so that a proximal portion of the cap remains projecting from the proximal end of the housing.

13. A syringe having means for adjustment for the dosage of liquid to be injected comprising:

a housing for receiving a container of liquid, the container of liquid having a close first end and a piston closing a second end of the container, the housing having a proximal end and a distal end, the distal end being adapted to receive a needle assembly for permitting liquid to pass out of the closed first end of the container, a plunger rod received within the housing for exerting a force on the piston closing the second of the container, the plunger rod having non-cylindrical cross-section, a first surface including threads, and a second surface, a collar received within the housing adjacent the container second end, the collar having a non-cylindrical opening corresponding generally to the cross-section of the plunger rod for preventing rotation of the plunger rod with respect to the housing and engaging means engaging the plunger rod second surface for restricting movement of the plunger rod toward the housing proximal end, a hollow cap enveloping the plunger rod end opposite the container and extending outward from the housing proximal end, the cap having a threaded interior surface rotatably engaging the plunger rod first surface portion for calibrated axial adjustment relative thereto and a distal end facing surface for contacting a stop fixed with respect to the housing upon movement of the cap and plunger rod toward the housing distal end, and a limit means for limiting the maximum calibrated movement of the hollow cap, used to adjust the dosage of liquid to be injected from the syringe.

14. The syringe of claim 13 wherein the collar comprises a radial outside surface frictionally engaging an inside surface of the housing, and distal end surface contacting the container of liquid for maintaining the container in fixed position with respect to the housing.

15. The syringe of claim 14 wherein the engaging means comprises a pair of opposed edges situated on opposite sides of the plunger road so as to prevent movement of the plunger rod toward the housing proximal end.

16. The improvement of claim 15 wherein the hollow cap further comprises a flexible member projecting outward from the cap and the housing further comprises a grooved interior surface, said flexible member engaging said grooved interior surface of the housing such that the calibrated relative adjustment causes sensible movement of the flexible member.

17. The syringe of claim 16 wherein the distal end facing surface comprises the distal end of the cap, and the stop comprises a land within the housing situated to contact the distal end of the cap so that a proximal portion of the cap remains projecting from the proximal end of the housing.

18. The improvement of claim 17 wherein the limit means comprises a threaded portion on an outer surface of the hollow cap and a follower adjustibly positioned on the threaded outer surface portion of the cap.

19. The improvement of claim 18 wherein the limit means further comprises a barrier element fixed with respect to the housing for limiting the length of movement of the hollow cap relative to the housing by contacting the adjustibly positioned follower.

20. The syringe of claim 19 further comprising a needle assembly coupled to the distal end of the housing and a safety shield enveloping the needle assembly.

21. The syringe of claim 20 further comprising a covering element enclosing the distal end of the housing and the safety shield, the covering element including a clip member extending along one side of the housing and cooperating therewith.

22. In a syringe having a housing for receiving a container of liquid, the housing having a proximal end and a distal end, the distal end being adapted to receive an injection needle assembly for permitting liquid to pass out of the closed first end of the container, an improved means for adjustment of the dosage of liquid to be injected comprising:

a plunger rod received within the housing for exerting a force on the piston closing the second of the container, the plunger rod having non-cylindrical cross-section, a first surface including threads, and a second surface, a collar received within the housing adjacent the container second end, the collar having a non-cylindrical opening corresponding generally to the cross-section of the plunger rod for preventing rotation of the plunger rod with respect to the housing and engaging means engaging the plunger rod second surface for restricting movement of the plunger rod toward the housing proximal end, a hollow cap enveloping the plunger rod end opposite the container and extending outward from the housing proximal end, the cap having a threaded interior surface rotatably engaging the plunger rod first surface portion for calibrated axial adjustment relative thereto and a distal end facing surface for contacting a stop fixed with respect to the housing upon movement of the cap and plunger rod toward the housing distal end, and threaded portion on an outer surface of the hollow cap and a follower adjustably positioned on the threaded outer surface portion of the cap to permit variation in the limit of the calibrated movement of the cap with respect to the plunger rod.

23. The improvement of claim 22 further comprising a barrier element fixed with respect to the housing for limiting the length of movement of the hollow cap relative to the housing by contacting the adjustibly positioned follower.

24. The improvement of claim 22 wherein the distal end facing surface comprises the distal end of the cap, and the stop comprises a land within the housing situated to contact the distal end of the cap so that a proximal portion of the cap remains projecting from the proximal end of the housing.

25. The improvement of claim 22 wherein the hollow cap further comprises a flexible member projecting outward from the cap and the housing further comprises a grooved interior surface, said flexible member engaging said grooved interior surface of the housing, the calibrated relative adjustment causing sensible movement of the flexible member.

26. The improvement of claim 22 wherein the engagement means comprises a pair of opposed pawls situated on opposite side of the plunger rod and the plunger rod further comprises a line of ratchet teeth on its second surface, said opposing pawls each engaging a line of ratchet teeth so as to prevent movement of the plunger rod toward the housing proximal end.

27. The improvement of claim 22 wherein the collar comprises a radial outside surface frictionally engaging an inside surface of the housing, and a distal end surface contacting the container of liquid for maintaining the container in fixed position with respect to the housing.

28. The improvement of claim 22 further comprising a scale on an outer surface of the cap for indicating a dose to be delivered by the syringe, the scale having a first end situated substantially at the housing proximal end when said distal end facing surface contacts said stop.

29. The improvement of claim 28 wherein the scale includes a stepped line spiralling from said first end toward the distal end of the cap, and indicia associated with at least selected steps of the line for indicating the dose to be delivered.

* * * * *

UNITED STATES PATENT AND TRADEMARK OFFICE
CERTIFICATE OF CORRECTION

PATENT NO. : 5,308,340

DATED : May 3, 1994

INVENTOR(S) : Dale C. Harris

It is certified that an error appears in the above-identified patent and that said Letters Patent is hereby corrected as shown below:

Claim 13, Column 8, line 48, delete "closing the second of the", and insert therefor --closing the second end of the--.

Claim 22, Column 9, line 52, delete "the piston closing the second of the", and insert therefor --a piston closing a second end of the--.

Claim 22, Column 10, line 7, delete "rotatably", and insert therefor --movably--.

Claim 22, Column 10, line 8, delete "axial".

Signed and Sealed this

First Day of November, 1994

Attest:

Attesting Officer

BRUCE LEHMAN

Commissioner of Patents and Trademarks